United States Patent [19]
Horwell et al.

[11] Patent Number: 6,133,307
[45] Date of Patent: Oct. 17, 2000

[54] CERTAIN BENZOFURANYL-N-[PYRROLIDIN-1-YL]-N-METHYL-ACETAMIDE DERIVATIVES USEFUL AS OPIOID AGONISTS

[75] Inventors: David Christopher Horwell, Cambridge; Simon Osborne, Suffolk, both of United Kingdom

[73] Assignee: Warner-Lambert Company, Morris Plains, N.J.

[21] Appl. No.: 09/341,027

[22] PCT Filed: Apr. 17, 1998

[86] PCT No.: PCT/US98/07832

§ 371 Date: Jun. 30, 1999

§ 102(e) Date: Jun. 30, 1999

[87] PCT Pub. No.: WO98/49141

PCT Pub. Date: Nov. 5, 1998

Related U.S. Application Data

[60] Provisional application No. 60/045,190, Apr. 30, 1997, and provisional application No. 60/078,045, Mar. 16, 1998.

[51] Int. Cl.[7] ................ C07D 207/14; C07D 401/12; A61K 31/4025
[52] U.S. Cl. ............... 514/422; 548/518; 546/284.1
[58] Field of Search .................. 548/518; 514/422

[56] References Cited

U.S. PATENT DOCUMENTS

| | | | |
|---|---|---|---|
| 4,145,435 | 3/1979 | Szmuszkovicz | 514/429 |
| 4,212,878 | 7/1980 | Lednicer et al. | 514/409 |
| 4,359,476 | 11/1982 | Kaplan et al. | 514/409 |
| 4,438,130 | 3/1984 | Kaplan | 514/210 |
| 4,663,343 | 5/1987 | Horwell et al. | 514/429 |
| 4,906,655 | 3/1990 | Horwell et al. | 514/422 |
| 5,688,955 | 11/1997 | Kruse et al. | 546/276.4 |

*Primary Examiner*—Alan L. Rotman
*Attorney, Agent, or Firm*—Elizabeth M. Anderson

[57] ABSTRACT

The novel compounds of formula (I) of the instant invention are selective kappa opioid agonists useful in the treatment of arthritis, hypertension, pain, inflammation, migraine, inflammatory disorders of the gastrointestinal tract, IBS, and psoriasis. The compounds, novel intermediates useful in their preparations and pharmaceutical compositions containing them, are part of the invention.

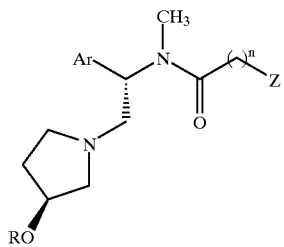

(I)

12 Claims, No Drawings

CERTAIN BENZOFURANYL-N-[PYRROLIDIN-1-YL]-N-METHYL-ACETAMIDE DERIVATIVES USEFUL AS OPIOID AGONISTS

CROSS REFERENCE

This application claims the benefit under 35 U.S.C. 119(e) of Provisional Application Ser. No. 60/045,190 filed Apr. 30, 1997 and Provisional Application Ser. No. 60/078,045 filed Mar. 16, 1998.

BACKGROUND OF THE INVENTION

The compounds covered below are selective kappa opioid agonists. These compounds and their salts are useful in the treatment of arthritis, hypertension, pain, particularly pain which is inflammatory in origin and post-operative pain, inflammation, migraine, inflammatory disorders of the gastrointestinal tract, Parkinsonism, and stroke.

These compounds with the (S)-hydroxyl group on the 3 position of the pyrrolidine ring are more potent kappa agonists in the rabbit vas deferens assay than those compounds lacking a hydroxyl and should, therefore, be more potent for the treatment of the above mentioned conditions.

SUMMARY OF THE INVENTION

The compounds are of the general structure:

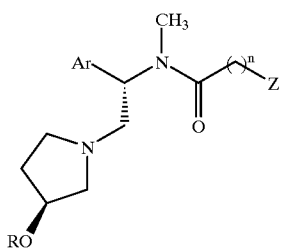

I or a pharmaceutically acceptable salt thereof wherein:
  Ar is phenyl unsubstituted or substituted with from 1 to 5 substituents selected from methyl, hydroxy, methoxy, and halogen;
  n is an integer of from 0 to 1;
  Z is 2-benzofuranyl, 3-benzofuranyl, 4-benzofuranyl, 5-benzofuranyl, 6-benzofuranyl, 7-benzofuranyl, 4-(methylsulphonyl)phenyl, 3-(methylsulphonyl)phenyl, when n is 1;
  Z is diphenylcyclopropene when n is 0; and
  R is hydrogen or methyl.

A pharmaceutical composition comprising a compound of Formula I in a therapeutically effective amount in combination with a pharmaceutically acceptable carrier in unit dosage form is another aspect of the instant invention.

The compounds of the invention are useful in the treatment of pain, inflammation, migraine, inflammatory disorders of the gastrointestinal tract, psoriasis, and irritable bowel syndrome (IBS).

Processes for the preparation of novel compounds are yet another aspect of the invention. The novel intermediates are still another aspect of the invention. They are:
  1-Benzyl-3-(tert-butyl-dimethyl-silanyl)-pyrrolidine;
  3-(tert-Butyl-dimethyl-silanyl)-pyrrolidine;
  {2-[3-(tert-Butyl-dimethyl-silanyloxy)-pyrrolidin-1-yl]-1-phenyl-ethyl}-methyl-amine; and
  2-Benzofuran-4-yl-N-{2-[3-(tert-butyl-dimethyl-silanyloxy)-pyrrolidin-1-yl]-1-phenyl-ethyl}-N-methyl-acetamide.

A novel process is a preparation of a compound of Formula I above which comprises:
  a.) converting styrene oxide into a diamine of formula 3

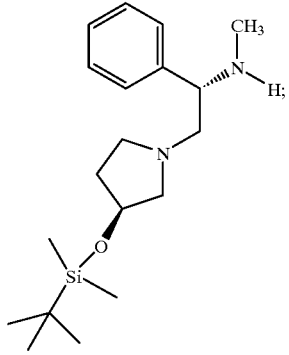

3 b.) coupling the diamine with an acid using a suitable coupling reagent to produce the corresponding amide;
  c.) removing the protecting group to produce the compound of formula 1, and converting it, if desired, to the pharmaceutically acceptable thereof.

DETAILED DESCRIPTION OF THE INVENTION

Selective kappa opioid agonists are selected from:

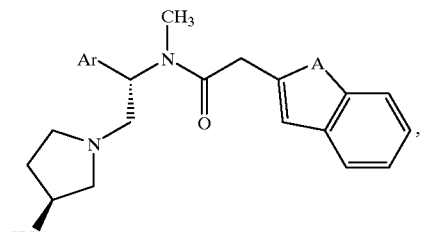

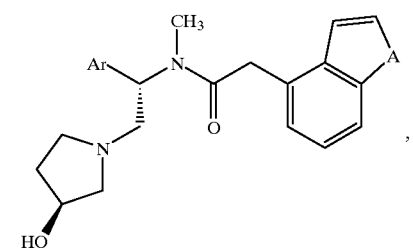

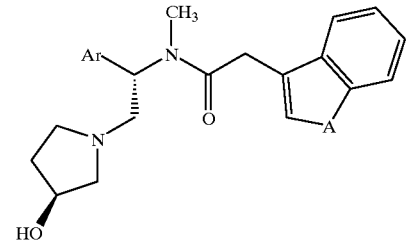

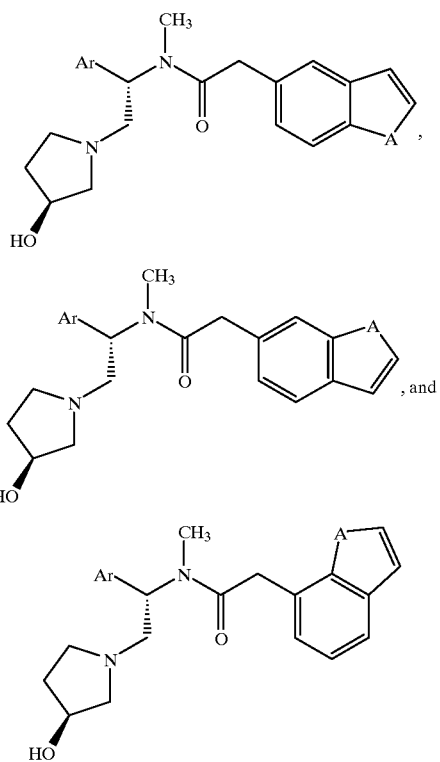

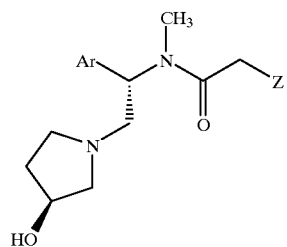

where:

Ar is phenyl or phenyl substituted with methyl, hydroxyl, methoxy, chloro, fluoro, iodo, or bromo, and Z is phenyl substituted with cyano, nitro, trifluoromethyl, halo, or dihalo, where halo is fluoro, chloro, bromo, or iodo.

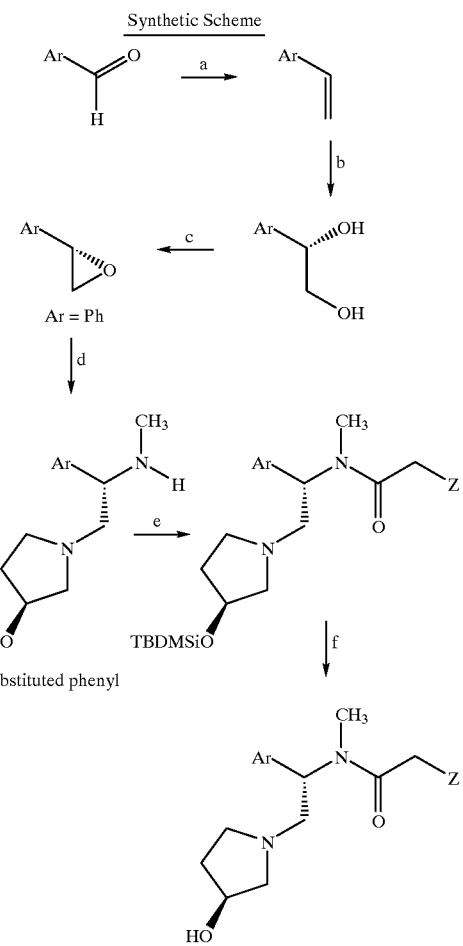

where:

A is oxygen or sulfur;

Ar is phenyl or phenyl substituted with methyl, hydroxyl, methoxy, chloro, fluoro, iodo, or bromo.

Other selective kappa opioid agonists are:

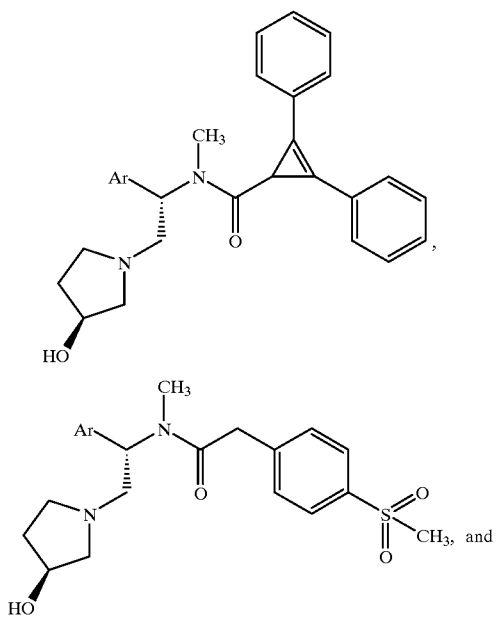

Reactions and conditions:
a) Ph₃P+CH₃Br, BuLi, THF, −20° C.;
b) AD-mix-α, H₂O-tBuOH;
c) Me₃SiCl, MeC(OMe)₃, CH₂Cl₂ then K₂CO₃, MeOH;
d) Pyrrolidine, ethanol, 90° C., then concentrate: ether, MeSO₂Cl, Et₃N, then MeNH₂ (aqueous);
e) CDl, ZCH₂CO₂H, THF;
f) TBAF

Synthesis of some key intermediates

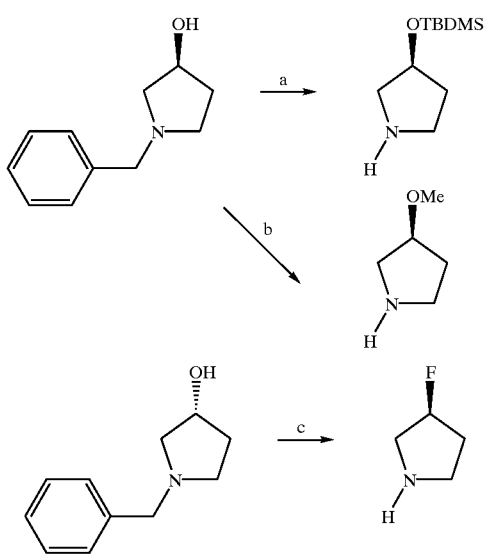

Reactions and conditions:

a) TBDMSiCl, imidazole, CH$_2$Cl$_2$; then Pd(OH)$_2$/C, H$_2$, EtOH;
b) MeI, NaH, THF; then Pd(OH)$_2$/C, H$_2$, EtOH;
c) KF, Ph$_3$P, DEAD, THF; then Pd(OH)$_2$/C, H$_2$, EtOH

Synthesis of Key Intermediates

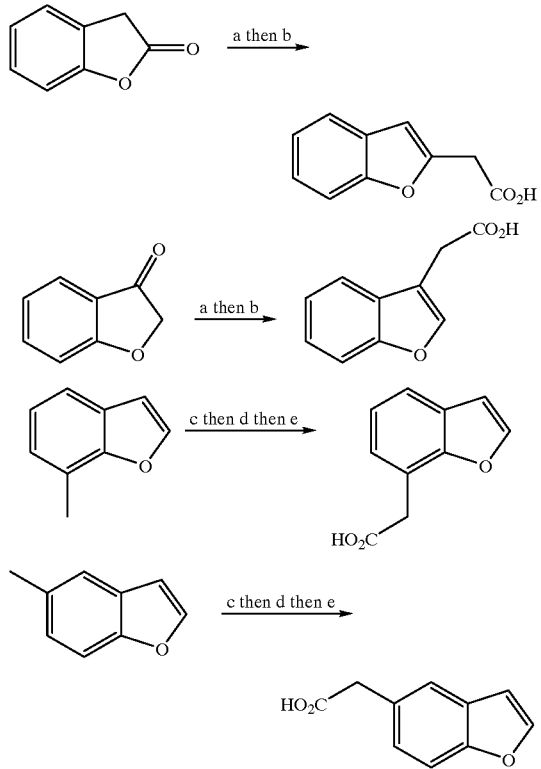

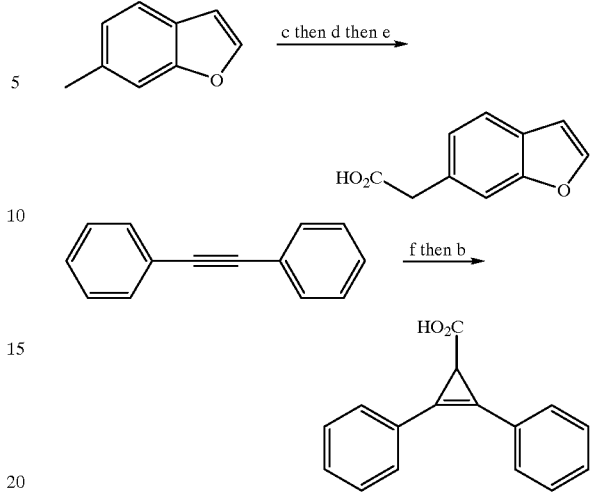

Reactions and conditions:

a) Ph$_3$P=CHCO$_2$Et, toluene, reflux;
b) LiOH, H$_2$O-MeOH;
c) NBS, (PhCO$_2$)$_2$, CCl$_4$, reflux;
d) KCN, DMF;
e) HCl, reflux;
f) Rh$_2$(OAc)$_4$,N$_2$CHCO$_2$Et Preferred compounds of the instant invention are those of Formula I wherein Z is 2-benzofuranyl, 3-benzofuranyl, 4-benzofuranyl, 5-benzofuranyl, 6-benzofuranyl, 7-benzofuranyl, 4-(methylsulphonyl)phenyl, 3-(methylsulphonyl)phenyl, and n is 1.

Other preferred compounds of the instant invention are those of Formula I wherein Z is diphenylcyclopropene and n is 0.

More preferred compounds are:

2-Benzofuran-4-yl-N-[2-(3-hydroxy-pyrrolidin-1-yl)-1-phenyl-ethyl]-N-methyl-acetamide;

2-Benzofuran-3-yl-N-[2-(3-hydroxy-pyrrolidin-1-yl)-1-phenyl-ethyl]-N-methyl-acetamide;

N-[2-(3-Hydroxy-pyrrolidin-1-yl)-1-phenyl-ethyl]-N-methyl-2-phenyl-acetamide; and 2-Benzofuran-4-yl-N-[2-(3-methoxy-pyrrolidin-1-yl)-1-phenyl-ethyl]-N-methyl-acetamide.

Another more preferred compound is 2,3-diphenyl-cycloprop-2-enecarboxylic acid [2-(3-hydroxy-pyrrolidin-1-yl)-1-phenyl-ethyl]-methyl amide.

Compounds of the present invention contain one or more asymmetric carbon atoms and therefore exist in various stereoisomeric forms. Additionally, the compounds of this invention exist in different geometric isomeric forms. The instant invention is all geometric and stereoisomeric forms.

The compounds of the present invention and/or their nontoxic, pharmaceutically acceptable acid addition salts may be administered to mammals in pharmaceutical compositions which comprise one or more compounds of this invention and/or salts thereof in combination with a pharmaceutically acceptable nontoxic carrier.

As parenteral compositions, the compounds of this invention may be administered with conventional injectable liquid carriers such as sterile, pyrogen-free water, sterile peroxide-free ethyl oleate, dehydrated alcohols, polypropylene glycol, and mixtures thereof.

Suitable pharmaceutical adjuvants for the injectable solutions include stabilizing agents, solubilizing agents, buffers, and viscosity regulators. Examples of these adjuvants include ethanol, ethylenediamine tetraacetic acid (EDTA), tartrate buffers, citrate buffers, and high molecular weight polyethylene oxide viscosity regulators. These pharmaceutical formulations may be injected intramuscularly, intraperitoneally, or intravenously.

As solid or liquid pharmaceutical compositions, the compounds of the present invention may be administered to mammals orally in combination with conventional compatible carriers in solid or liquid form. These orally administered pharmaceutical compositions may contain conventional ingredients such as binding agents such as syrups, acacia, gelatin, sorbitol, tragacanth, polyvinylpyrrolidone, and mixtures thereof.

The compositions may further include fillers such as lactose, mannitol, starch, calcium phosphate, sorbitol, methylcellulose, and mixtures thereof.

These oral compositions may also contain lubricants such as magnesium stearate, high molecular weight polymers such as polyethylene glycol, high molecular weight fatty acids such as stearic acid, silica, or agents to facilitate disintegration of the solid formulation such as starch, and wetting agents such as sodium lauryl sulfate.

The oral pharmaceutical compositions may take any convenient form such as tablets, capsules, lozenges, aqueous or oily suspensions, emulsions, or even dry powders which may be reconstituted with water or other suitable liquids prior to use.

The solid or liquid forms may contain flavorants, sweeteners, and/or preservatives such as alkyl p-hydroxybenzoates. The liquid forms may further contain suspending agents such as sorbitol, glucose, or other sugar syrups, methyl-, hydroxymethyl-, or carboxymethylcellulose, and gelatin, emulsifying agents such as lecithin or sorbitol monooleate, and conventional thickening agents. The liquid compositions may be encapsulated in, for example, gelatin capsules.

As topically administered pharmaceutical compositions, the compounds of the present invention may be administered in the form of ointments or creams containing from about 0.1% to about 10% by weight of the active component in a pharmaceutical ointment or cream base.

Compounds of the present invention may be rectally administered in the form of suppositories. For preparing suppositories a low-melting wax such as a mixture of fatty acid glycerides or cocoa butter is first melted, and the active ingredient is dispersed homogeneously in the melt. The mixture is then poured into convenient sized molds and allowed to cool and solidify.

Preferably, the pharmaceutical compositions of this invention are in unit dosage form. In such form, the preparation is subdivided into unit doses containing appropriate amounts of the active component. The unit dosage can be a packaged preparation with the package containing discrete quantities of the preparation. For example, the package may take the form of packaged tablets, capsules, and powders in envelopes, vials, or ampoules. The unit dosage form can also be a capsule, cachet, or tablet itself or can be the appropriate number of any of these packaged forms.

The quantity of active compound in the unit dosage form may be varied or adjusted from about 0.5 mg to about 350 mg according to the particular application and the potency of the active ingredient.

When employed systematically in therapeutic use as pharmacologic agents in the pharmaceutical methods of this invention, the compounds are administered at doses of from about 0.05 mg to about 2.0 mg of active compound per kilogram of body weight of the recipient.

The rabbit vas deferens is a specific test for activity at the K-receptor and allows comparison of potency and efficacy of a test ligand and its parent K-agonist. Rabbit vas deferens assay (Oka T., Negiski K. et al., *Eur. J. Pharmacol.*, 1981;73:235) was used to test the compounds of the invention. One of the compounds of the invention, the compound of Example 4, 2,3-diphenyl-cycloprop-2-enecarboxylic acid methyl-(7-pyrrolidin-1-yl-1-oxa-spiro[4.5]dec-8-yl)-amide, exhibited agonist functional activity of $EC_{50}(LVD)=12$ nM.

The relative potency of compounds in the rabbit vas deferens assay is given in Table 1 below. The compounds of invention are on the left side, with reference compounds on the right side. The potency is the $EC_{50}$ of the compound/$EC_{50}$ of [5R-(5α,7α,8β)]-N-methyl-N-[7-(1-pyrrolidinyl)-1-oxaspiro-[4,5]dec-8-yl]-4-benzofuranacetamide, monohydrochloride.

TABLE 1

| Invention Compounds | | Reference Compounds | |
|---|---|---|---|
| Compound 5 | 0.28 | Compound 12 | 6.92 |
| Compound 16 | 1.17 | Compound 12 | 6.92 |
| Compound 6 | 1.5 | Compound 11 | 1.43 |
| Compound 7 | 0.056 | Compound 13 | 1.18 |
| Compound 8 | 1.6 | Compound 14 | 21.1 |
| Compound 9 | 0.04 | Compound 15 | 1.38 |

The results of the testing shown in Table 1 above show that the compounds of the invention are kappa opioid agonists and thus are useful in the treatment of arthritis, hypertension, pain (particularly pain which is inflammatory in origin and post-operative pain), inflammation, migraine, and inflammatory disorders of the gastrointestinal tract, IBS, and psoriasis.

Synthesis of key intermediates

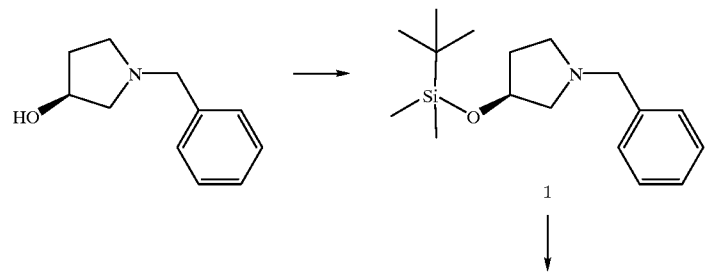

1

↓

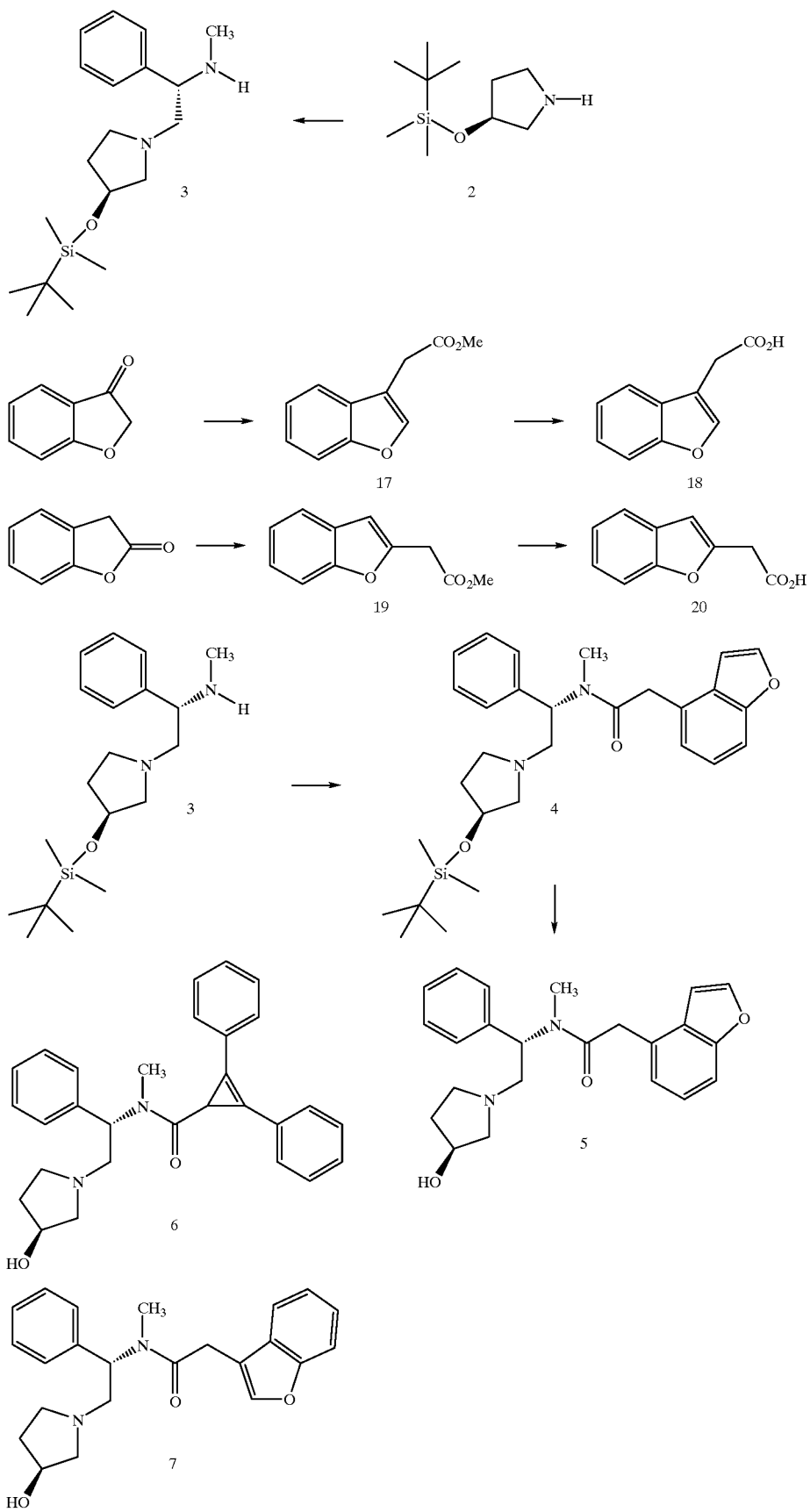

-continued
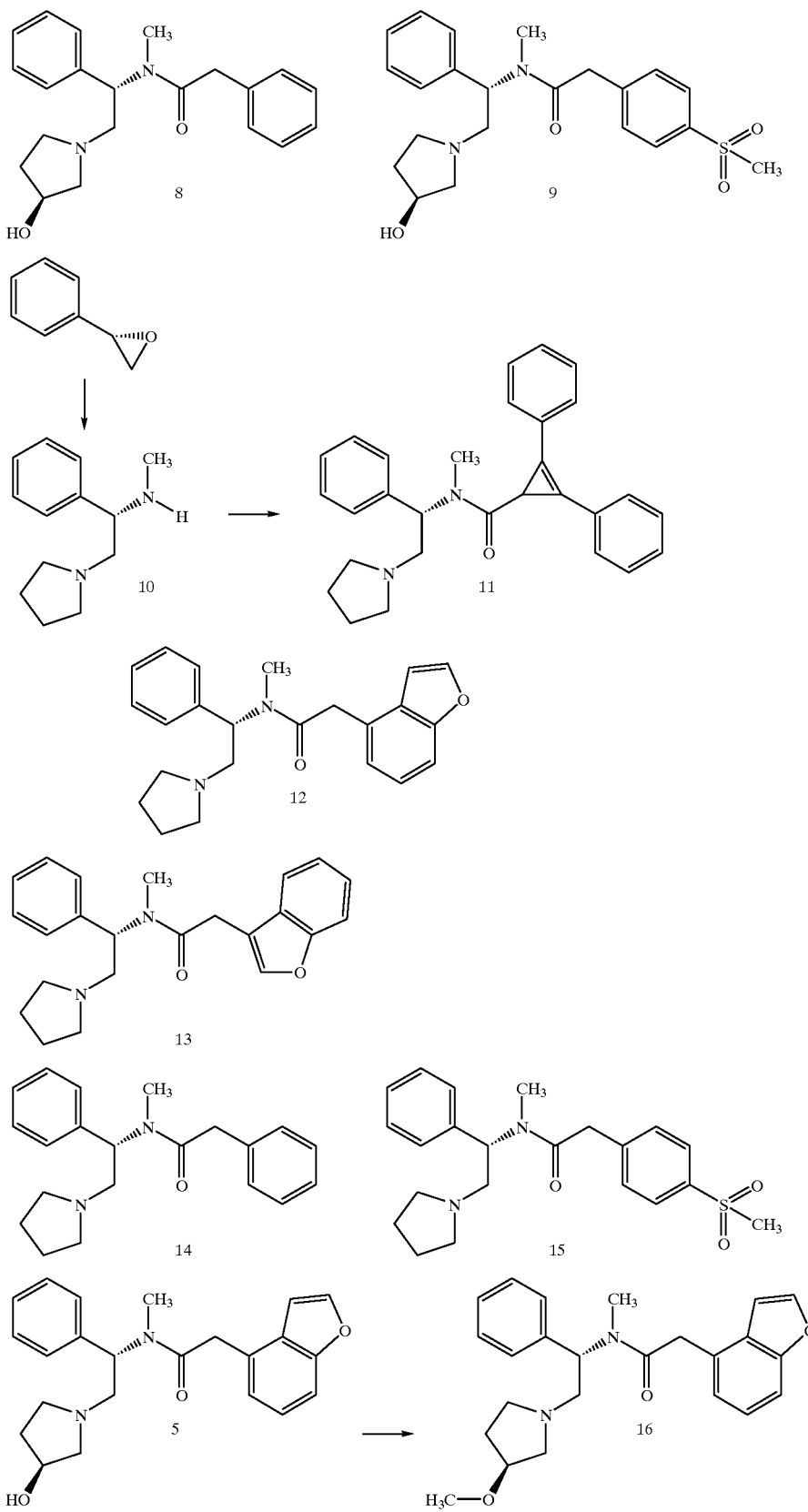

The above compounds (11, 12, 13, 14, and 15) are the reference compounds found in Table 1.

The following examples are illustrative of the instant invention and are not intended to limit its scope in any way.

EXAMPLE 1
1-Benzyl-3-(tert-butyl-dimethyl-silanyl)-pyrrolidine

To a solution of t-butyldimethylsilyl chloride (15 g, 100 mmol) in dichloromethane (30 mL) under argon, imidazole (8.7 g, 128 mmol) in dichloromethane (30 mL) was added, followed by S-(−)-1-benzyl-3-pyrrolidinol (15 g, 85 mmol) in dichloromethane (15 mL). The reaction was stirred at room temperature for 4 hours, then poured into water (300 mL) and extracted with dichloromethane (3×300 mL). The organics were dried ($MgSO_4$) and the solvent removed in vacuo. Column chromatography (ethyl acetate:heptane 4:1→ethyl acetate 100%) gave the product as a yellow oil, 85 mmol, 100%.

$^1$H NMR (400 MHz, $CDCl_3$): δ7.28–7.18 (5H, m); 4.38–4.33 (1H, m); 3.62 (1H, d, J=12.8 Hz); 3.54 (1H, d, J=12.8 Hz); 2.87 (1H, dd, J=9.6, 6.4 Hz); 2.63–2.52 (2H, m); 2.29 (1H, dd, J=9.6, 4.8 Hz); 2.12–2.03 (1H, m); 1.69–1.63 (1H, m); 0.87 (9H, s); 0.03 (3H, s); 0.02 (3H, s).

EXAMPLE 2
3-(tert-Butyl-dimethyl-silanyl)-pyrrolidine

To a solution of compound 15 (24.78 g, 85 mmol) in ethanol (200 mL) was added palladium catalyst (10% on carbon) (6.0 g) and HCl (4 M in dioxane) (4.5 mL, 18 mmol). This was hydrogenated at 30° C. for 6 hours and then filtered through Celite. The solvent was removed in vacuo, and column chromatography (ethyl acetate:methanol:ammonia 40:9:1) gave the product as a yellow oil, 82 mmol, 96%. $^1$H NMR (400 MHz, $CDCl_3$): δ4.38–4.35 (1H, m); 3.18–3.12 (1H, m); 2.95–2.87 (3H, m); 1.90–1.86 (1H, m); 1.72–1.70 (1H, m); 0.88 (9H, s); 0.06 (6H,s).

MS($ES^+$)=202.22.

$C_{10}H_{24}NOSi^+$ requires 202.40.

IR (thin film) υ=2930.0, 1417.0, 1254.0.

EXAMPLE 3
{2-[13-(tert-Butyl-dimethyl-silanyloxy)-pyrrolidin-1-yl]-1-phenyl-ethyl}-methyl-amine Compound 17 (5.75 g, 18 mmol) was dissolved in diethyl ether (80 mL) (O'Brien et al., *Tetrahedron Letters*, 1996;37:5619–5622), cooled to 0° C. and flushed with argon. Triethylamine (7.6 mL, 55 mmol) was added followed by methanesulphonyl chloride (1.6 mL, 21 mmol), and the reaction was stirred for 30 minutes. More triethylamine (5.1 mL, 37 mmol) was added, and the reaction was warmed to room temperature over 30 minutes before an aqueous solution of methylamine (40% w/w) (27 mL, 313 mmol) and water (22 mL) were added. After stirring for 22 hours, the layers were separated, and the aqueous layer was extracted with diethyl ether (3×150 mL). The combined organics were washed with 5% sodium bicarbonate solution (90 mL), water (90 mL) and brine (90 mL), dried ($MgSO_4$), and the solvent removed in vacuo. Purification by column chromatography (dichloromethane:methanol 9:1) gave the product as a yellow semi-solid, 15 mmol, 81%.

$^1$H NMR (400 MHz, $CDCl_3$): δ7.38–7.24 (5H, m); 4.42–4.36 (1H, m); 3.61 (1H, dd, J=10.4, 3.6 Hz); 3.05 (1H, dd, J=9.6, 6.0 Hz); 2.85 (1H, t, J=11.6 Hz); 2.77 (1H, dd, J=16.4, 8.0 Hz); 2.69–2.61 (1H, m); 2.41 (1H, dd, J=12.4, 3.2 Hz); 2.35 (1H, dd, J=9.6, 4.0 Hz); 2.31 (3H, s); 2.17–2.03 (1H, m); 1.72–1.65 (1H, m); 0.89 (9H, s); 0.06 (6H, s).

MS($ES^+$)=335.15.

$C_{19}H_{35}N_2OSi^+$ requires 335.59.

IR (thin film) υ=2954.0, 2856.0, 2790.0, 2686.0, 1597.0, 1472.0, 1463.0, 1256.0.

EXAMPLE 4
2-Benzofuran-4-yl-N-{2-[3-(tert-butyl-dimethyl-silanyloxy)-pyrrolidin-1-yl]-1-phenyl-ethyl}-N-methyl-acetamide To a solution of benzofuran-4-acetic acid (0.17 g, 0.95 mmol) in tetrahydrofuran (2.5 mL) was added carbonyl diimidazole (0.16 g, 1.00 mmol). The reaction was stirred at room temperature under argon for 3.5 hours, then the solvent was removed in vacuo. Compound 18 (0.30 g, 0.90 mmol) in tetrahydrofuran (2.0 mL) was added and the reaction stirred for 19.5 hours at room temperature under argon. The solvent was removed in vacuo, and the residue was dissolved in ethyl acetate (25 mL) and washed with saturated sodium hydrogen carbonate solution (7 mL), water (7 mL) and brine (7 mL). The organics were dried ($MgSO_4$) and the solvent removed in vacuo. Column chromatography (dichloromethane:methanol 19:1 followed by ethyl acetate, 100%) gave the product as a yellow oil, 0.43 mmol, 48%.

$^1$H NMR (400 MHz, $CDCl_3$): δ7.61 (1H, d, J=2.0 Hz); 7.41–7.13 (8H, m); 7.02 (1H rotamer, br); 6.89 (1H dd, J=2.0, 0.8 Hz); 6.10 (1H, dd, J=10.8. 5.2 Hz); 5.07–5.03 (1H rotamer, m); 4.37–4.28 (1H, m); 4.23 (1H rotamer, br); 4.08–3.92 (2H, m); 3.13–3.07 (1H, m); 3.00–2.93 (1H, m); 2.88–2.66 (2H, m); 2.82 (3H rotamer, s); 2.72 (3H, s); 2.59–2.53 (1H, m); 2.49–2.45 (1H rotamer, m); 2.37 (1H, dd, J=9.6, 4.4 Hz); 2.23 (1H rotamer, dd, J=9.6, 4.4 Hz); 2.09–1.91 (1H, m); 1.68–1.63 (1H, m); 0.088 (9H, s); 0.04 (3H, s); 0.03 (3H, s).

MS($ES^+$)=493.08.

$C_{29}H_{41}N_2O_3Si^+$ requires 493.75.

EXAMPLE 5
2-Benzofuran-4-yl-N-[2-(3-hydroxy-pyrrolidin-1-yl)-1-phenyl-ethyl]-N-methyl-acetamide To a solution of compound 19 (0.21 g, 0.43 mmol) in tetrahydrofuran (5 mL) was added tetrabutylammonium fluoride (1.0 M in tetrahydrofuran) (0.43 mL, 0.43 mmol). The reaction was stirred at room temperature under argon for I hour before being poured into water (5 mL). Brine (20 mL) was added and the reaction mixture extracted with dichloromethane (3×20 mL). The organics were dried ($MgSO_4$) and the solvent removed in vacuo. Column chromatography (dichloromethane:methanol 9:1 →4:1) gave a residue, which was dissolved in methanol (2 mL) and saturated sodium hydrogen carbonate solution (2 mL) was added. This was stirred at room temperature for 18 hours, then poured into water (5 mL) and brine (10 mL). The solution was extracted with dichloromethane (3×20 mL), dried ($MgSO_4$), and concentrated in vacuo. Column chromatography (dichloromethane:methanol 9:1) gave a clear oil, which was converted to the HCl salt by dissolving in dichloromethane (0.5 mL) and adding 0.5 mL HCl in diethyl ether (1 mL). The solvent was removed in vacuo to give a white solid which was washed with ethyl acetate to give the product, 0.1 5 mmol, 35%.

$^1$H NMR (400 MHz, DMSO): δ7.94 (1H, dd, J=10.0, 2.0 Hz); 7.48–7.45 (1H, m); 7.40–7.31 (3H, m); 7.26–7.21 (3H, m); 7.14–7.11 (2H, m); 6.19–6.15 (1H, m); 4.45–4.43 (1H, m); 4.22–4.00 (3H, m); 3.70–3.66 (2H, m); 3.58–3.50 (1H, m); 3.39–3.26 (2H, m); 3.32 (3H, s); 2.36–2.14 (1H, m); 1.93–1.85 (1H, m).

IR (thin film) υ=3210.6, 1645.0, 1432.8, 1391.5.

Analysis Expected: C, 66.5; H, 6.56; N, 6.75.

Obtained: C, 66.4; H, 6.44; N, 6.48.

Melting point 168–182° C.
MS(ES⁺)=379.06.
$C_{23}H_{27}N_2O_3^+$ requires 379.48.
Examples 6, 7, 8, and 9 prepared in an identical manner to Example 5.

EXAMPLE 6
2,3-Diphenyl-cycloprop-2-enecarboxylic acid [2-(3-hydroxy-pyrrolidin-1-yl)-1-phenyl-ethyl]-methyl-amide $^1$H NMR (400 MHz, CDCl₃): δ7.97 (2H, m); 7.61–7.56 (2H, m); 7.52–7.21 (10.5H, m); 7.08 (0.5H, br); 6.35–6.29 (1H, m); 5.51–5.49 (0.5H, m); 4.48 (0.5H, br); 4.18–4.15 (1.5H, m); 4.01–3.98 (1H, m); 3.56 (0.5H, br); 3.34–3.23 (5H, m); 3.01 (1H, br); 2.76 (1H, br); 2.44–2.43 (1H, m); 2.28–2.26 (1H, m).

IR (thin film) υ=3852.0, 3193.0, 1634.0, 1442.0.
Analysis Expected: C, 73.3; H, 6.58; N. 5.90.
Obtained: C, 72.7; H, 6.40; N, 5.94.
MS(ES⁺)=473.02.
$C_{29}H_{33}N_2O_4^+$ requires 473.60.
Melting point 130–134° C.

EXAMPLE 7
2-Benzofuran-3-yl-N-[2-(3-hydroxy-pyrrolidin-1-yl)-1-phenyl-ethyl]-N-methyl-acetamide $^1$H NMR (400 MHz, CDCl₃): δ11.97–7.60 (2H, m); 7.46 (1H, d, J=8.0 Hz); 7.35–7.09 (7H, m); 6.47–6.40 (1H, m); 5.39 (0.6H, d, J=11.2 Hz); 4.56–4.48 (1H, m); 4.37 (0.6H, br); 4.24–4.16 (1H, m); 4.07–3.97 (1.6H, m); 3.92–3.82 (1.6H, m); 3.50–3.47 (0.4H, m); 3.33–3.25 (0.8H, m); 3.14 (0.6H, br); 3.01 (1H, br); 2.95 (1.8H, s); 2.93 (1.2H, s); 2.81 (0.6H, br); 2.51 (0.8H, br); 2.39–2.37 (1H, m); 2.04–2.00 (0.4H, m).

IR (thin film) υ=3364.0, 1645.0, 1454.0, 1395.4.
Analysis Expected: C, 66.5; H, 6.56; N, 6.75.
Obtained: C, 66.4; H, 6.40; C, 6.70.
MS(ES⁺)=379.16.
$C_{23}H_{27}N_2O_3^+$ requires 379.48.

EXAMPLE 8
N-[2-(3-Hydroxy-pyrrolidin-1-yl)-1-phenyl-ethyl]-N-methyl-2-phenyl-acetamide IR (thin film) υ=3218.0, 1661.0, 1392.3.
Analysis Expected (1.0 HCl): C, 67.2; H. 7.26; N, 7.47.
Obtained: C, 66.9; H, 7.05; N, 7.65.
Melting point 134–139° C.
MS(ES⁺)=339.12.
$C_{21}H_{27}N_2O_2^+$ requires 339.46.

EXAMPLE 9
N-[2-(3-Hydroxy-pyrrolidin-1-yl)-1-phenyl-ethyl]-2-(4-methanesulfonyl-phenyl)-methyl-acetamide $^1$H NMR (400 MHz, DMSO): δ7.88–7.85 (2H, m); 7.58–7.54 (2H, m); 7.42–7.33 (3H, m); 7.28–7.24 (2H, m); 6.16 (1H, d, J=12.0 Hz); 5.56 (1H, d, J=5.2 Hz); 5.42 (1H, d, J=3.6 Hz); 4.46–4.42 (1H, m); 4.00–3.90 (2H, m); 3.71–3.68 (2H, m); 3.58–3.48 (1H, m); 3.38–3.28 (1H, m); 3.21 (3H, s); 3.19–3.15 (1H, m); 2.82 (3H, d, J=8.4 Hz); 2.33–2.27(1H, m); 2.18–2.14 (1H, m); 1.93–1.88 (1H, m).

IR (thin film) υ=1645.0, 1390.5, 1292.5, 1144.0.
Analysis Expected (1.4 HCl): C, 56.5; H, 6.34; N, 5.99.
Obtained: C, 56.4; H, 6.26; H, 6.11.
MS(ES⁺)=417.08.
$C_{22}H_{29}N_2O_4S^+$ requires 417.55.

Experimental for compounds synthesized for comparison of biological activity; see reference compounds in Table 1.

EXAMPLE 10
Methyl-(1-phenyl-2-pyrrolidinyl-1-yl-ethyl)-amine

See O'Brien et al., *Tetrahedron Letters*, 1996;37:5619–5622.

EXAMPLE 11
2,3-Diphenyl-cycloprop-2-enecarboxylic acid methyl-(1-phenyl-2-pyrrolidin-1-yl-ethyl)-amide To a solution of compound 6 (0.29 g, 1.42 mmol) in tetrahydrofuran (3.5 mL) was added triethylamine (0.20 mL, 1.43 mmol). At 0° C. and under argon, ethylchloroformate (0.11 mL, 1.15 mmol) was added. The reaction was stirred for 2.5 hours at 0° C., and then at room temperature for 1 hour. Compound 1 (0.27 g, 1.14 mmol) was dissolved in tetrahydrofuran (1.5 mL) and added to the reaction mixture. The reaction was stirred at room temperature for 21 hours, then poured into ethyl acetate (70 mL) and washed with saturated sodium hydrogen carbonate solution (15 mL), water (15 mL) and brine (15 mL). The organics were dried (MgSO₄) and concentrated in vacuo. Column chromatography (dichloromethane:methanol 9:1 followed by ethyl acetate 100% →ethyl acetate:methanol 9:1) gave the product as a yellow solid. This was converted to the HCl salt by dissolving in dichloromethane (1 mL) and adding HCl in diethyl ether (0.5 M) (2 mL). Removal of the solvent in vacuo gave a white solid.

IR (thin film)υ=3419.0, 2968.0, 1630.0, 1444.0, 839.0.
Analysis Expected (1.2 HCl): C, 74.6; H, 6.74; N, 6.01.
Obtained: C, 74.6; H, 6.63; N, 6.07.
MS(ES⁺)=423.06.
$C_{29}H_{31}N_2O^+$ requires 423.58.
Melting point 237–240° C.

EXAMPLE 12
2-Benzofuran-4-yl-N-methyl-N-(1-phenyl-2-pyrrolidin-1-yl-ethyl)-acetamide To a solution of benzofuran-4-acetic acid (1.29 g, 7.3 mmol) in dichloromethane (10 mL) was added triethylamine (2.0 mL, 14.6 mmol) and PyBroP (2.12 g, 6.6 mmol). This was stirred for 2 minutes, then a solution of compound 1 (1.20 g, 5.8 mmol) in dichloromethane (10 mL) was added. After 2 hours, the reaction mixture was poured into ethyl acetate (350 mL) and washed with saturated sodium hydrogen carbonate solution (80 mL), water (80 mL) and brine (80 mL). The organics were dried (MgSO₄) and the solvent removed in vacuo. Column chromatography (ethyl acetate:methanol 9:1) gave brown oil which was washed with a dichloromethane/diethyl ether mixture. The washings were concentrated in vacuo to give a yellow oil which was converted to the HCl salt by dissolving in dichloromethane (2 mL) and adding 4 M HCl in dioxane (1 mL). Washing with diethyl ether resulted in an off-white solid.

$^1$H NMR (400 MHz, CDCl₃): δ7.61 (1H, d, J=2.0 Hz); 7.41–7.11 (9H, m); 6.33 (1H, dd, J=12.0, 3.2 Hz); 4.31 (1H, d, J=16.0 Hz); 4.07–4.01 (3H, m); 3.24 (1H, d, J=12.8 Hz); 2.92 (4H, br); 2.34–2.24 (1H, br); 2.09–2.04 (1H, m); 1.58 (5H, br).

IR (thin film) υ=3417.0, 1644.0.
Analysis Expected (1.6 HCl): C, 65.6; H, 6.61; N, 6.66.
Obtained: C, 65.6; H, 6.57; N, 6.56.
MS(ES⁺)=363.11.
$C_{23}H_{27}N_2O_2^+$ requires 363.49.
Melting point 146–150° C.

Compounds 14, 16, and 17 synthesized in an identical manner to compound 13.

EXAMPLE 13
2-Benzofuran-3-yl-N-methyl-N-(1-phenyl-2-pyrrolidin-1-yl-ethyl)-acetamide $^1$H NMR (400 MHz, CDCl$_3$): δ12.13 (1H, s); 7.72–7.70 (1H, m); 7.60 (1H, s); 7.46–7.44 (1H, m); 7.38–7.18 (7H, m); 6.39 (1H, dd, J=12.0, 3.2 Hz); 4.20–4.16 (1H, m); 4.13–3.98 (3H, m); 3.93–3.89 (1H, m); 3.26–3.20 (1H, m); 2.99 (3H, s); 2.96–2.81 (2H, m); 2.40–2.25 (2H, m); 2.08–1.99 (2H, m).

IR (thin film) υ=3405.0, 2957.0, 2599.0, 1645.0, 1453.0, 1397.0, 1267.0.

Analysis

Expected (1.8 HCl): C, 64.5; H, 6.55; N, 6.54.
Obtained: C, 64.6; H, 6.73; N, 6.51.
Melting point 208–212° C.
MS(ES$^+$)=363.15.
C$_{23}$H$_{27}$N$_2$O$_2^+$ requires 363.49.

EXAMPLE 14
(S)-N-Methyl-2-phenyl-N-(1-phenyl-2-pyrrolidin-1-yl-ethyl)-acetamide Free base:

$^1$H NMR (400 MHz, CDCl$_3$): δ7.52–7.22 (10H, m); 6.13 (1H, dd, J=10.7. 5.6 Hz); 5.07 (1H, minor rotamer); 3.90–3.74 (2H, m); 3.13 (1H, dd, J=12.2, 10.7 Hz); 3.02–2.86 (2H, minor rotamer); 2.79–2.40 (8H, m); 1.78–1.70 (4H, m).

HCl salt: +0.2 H$_2$O requires: C, 69.58; H, 7.34; N, 7.73.
Found: C, 69.75; H, 7.66; N, 7.65.
Melting point 232–235° C.
HPLC Water (+0.1% TFA)/acetonitrile (+0.1% TFA) 80:20 to 20:80 over 20 minutes.
Room temperature=14.27.

EXAMPLE 15
(S)-2-(4-Methanesulfonyl-phenyl)-N-methyl-N-(1-phenyl-2-pyrrolidin-1-yl-ethyl)-acetamide $^1$H NMR (400 MHz, CDCl$_3$): δ12.07 (1H, br); 7.89 (2H, d, J=7.8 Hz); 7.61 (2H, d, J=7.8 Hz); 7.42–7.37 (3H, m); 7.21 (2H, m); 6.40 (1H, dd, J=10.0, ?? Hz); 4.42 (1H, d, J=16.4 Hz); 4.09–3.97 (3H, m); 3.78 (1H, d, J=16.4 Hz); 3.21 (1H, m); 3.05 (3H, s); 2.95 (3H, s); 2.95–2.87 (1H, m); 2.40–2.25 (2H, m); 2.08–2.05 (2H, m).

Required: C, 65.97; H, 7.04; N, 6.99.
Found: C, 65.40; H, 6.97; N. 7.32.

EXAMPLE 16
2-Benzofuran-4-yl-N-[2-(3-methoxy-pyrrolidin-1-yl)-1-phenyl-ethyl]-N-methyl-acetamide To a solution of compound 20 (1.06 g, 2.8 mmol) in tetrahydrofuran (5 mL) at 0° C. under argon was added sodium hydride (60% in mineral oil) (0.11 g, 2.8 mmol), followed by methyl iodide (0.17 mL, 2.8 mmol). After 1 hour, more sodium hydride (0.06 g, 1.4 mmol) and methyl iodide (0.09 mL, 1.4 mmol) were added. After another 1 hour, the reaction mixture was warmed to room temperature and saturated sodium hydrogen carbonate solution (100 mL) was added. The reaction mixture was extracted with dichloromethane (3×100 mL), dried (MgSO$_4$), and concentrated in vacuo. Column chromatography (ethyl acetate:methanol 9:1→ethyl acetate:methanol:ammonia 90:9:1) gave an impure residue which was purified using an automated column ([ethyl acetate:methanol:ammonia 40:9:1]:heptane 20:80→40:60 over 30 minutes, then 40:60 for 15 minutes). This gave a residue, 0.3 mmol, 12%, which was converted to the HCl salt by adding 1 M HCl in ethyl acetate (2 mL) and removing the solvent in vacuo.

$^1$H NMR (400 MHz, CDCl$_3$): δ7.61–7.60 (1H, m); 7.41–7.00 (9H, m); 6.39 (1H, dd, J=12.0, 2.8 Hz); 4.39–4.34 (1H, m); 4.13–4.05 (3H, m); 3.97–3.89 (2H, m); 3.42–3.34 (1H, m); 3.28 (3H, s); 3.26 (1H, br); 3.15–3.11 (1H, m); 2.91 (3H, s); 2.45–2.36 (1H, m); 2.19 (1H, dd, J=13.6, 6.0 Hz).

IR (thin film) υ=3419.0, 1634.0, 1431.0, 1394.0, 1246.0.
Analysis Expected (1.1 HCl): C, 66.3; H, 6.78; N, 6.48.
Obtained: C, 66.6; H, 6.61; N, 6.51.
HPLC acetonitrile/0.1% TFA in water/0.1% TFA 20→100% over 20 minutes.
Room temperature=13.17 minutes.
Melting point 177–182° C.
MS(ES$^+$)=393.19.
C$_{24}$H$_{29}$N$_2$O$_3^+$ requires 393.51.

Synthesis of intermediates:

For synthesis of Examples 17, 18, 19, and 20 (Elix et al., *Synthetic Communications*, 1972;2(6):409–414.

EXAMPLE 17
Benzofuran-3-yl-acetic acid methyl ester

A solution of 3-coumaranone (5.0 g, 37 mmol) and methyl(triphenylphosphoranylideneacetate) (13.5 g, 40 mmol) in toluene (70 mL) was heated to reflux for 25 hours. More toluene was added (50 mL), and after a further 5 hours, more methyl(triphenylphosphoranylideneacetate) (0.5 g, 1.5 mmol). After another 19 hours, a further 1.0 g (3.0 mmol) was added, and after a further 21 hours, the solvent was removed in vacuo. Column chromatography (heptane:ethyl acetate 4:1) gave the product as a brown oil, 33 mmol, 89%.

$^1$H NMR (400 MHz, CDCl$_3$): δ7.63 (1H, s); 7.58–7.47 (2H, m); 7.33–7.24 (2H, m); 3.73 (3H, s); 3.72 (2H, s).

EXAMPLE 18
Benzofuran-3-yl-acetic acid

A solution of compound 6 (6.23 g, 33 mmol) and lithium hydroxide monohydrate (1.45 g, 35 mmol) in tetrahydrofuran (50 ml,), water (35 mL), and methanol (14 mL) was stirred for 6.5 hours at room temperature. Water (70 mL) was added, and the reaction mixture was acidified to pH 4 using 2 M HCl and extracted with dichloromethane (5×200 mL). The organics were dried (MgSO$_4$) and the solvent removed in vacuo to give a brown solid. This was dissolved in diethyl ether, heptane was added, and the mixture was stirred overnight. Solvent was removed by syringe to give product as a pale brown solid, 27 mmol, 80%.

$^1$H NMR (400 MHz, CDCl$_3$): δ7.64 (1H, s); 7.58–7.56 (1H, m); 7.50–7.48 (1H, m); 7.34–7.24 (2H, m); 3.76 (2H, s).

EXAMPLE 19
Benzofuran-2-yl-acetic acid methyl ester

A solution of 2-coumaranone (5.0 g, 37 mmol) and methyl(triphenylphosphoranylideneacetate) (13.5 g. 40 mmol) in toluene (70 mL) was heated to reflux for 25 hours. More toluene was added (10 mL), and after a further 5 hours, more methyl(triphenylphosphoranylideneacetate) (0.5 g, 1.5 mmol). After another 19 hours, a further 1.0 g (3.0 mmol) was added, and after a further 21 hours, the solvent was removed in vacuo. Column chromatography (heptane:ethyl acetate 4:1) gave the product as a brown oil, 28 mmol, 75%.

$^1$H NMR (400 MHz., CDCl$_3$): δ7.53–7.43 (2H, m); 7.27–7. 8 (2H, m); 6.63 (1H, s); 3.84 (2H, s); 3.76 (3H, s).

EXAMPLE 20
Benzofuran-2-yl-acetic acid

A solution of compound 8 (5.32 g, 28 mmol) and lithium hydroxide monohydrate (1.24 g, 30 mmol) in tetrahydrofuran (45 mL), water (30 mL), and methanol (12 mL) was stirred for 5 hours at room temperature. Water (60 mL) was added, and the reaction mixture was acidified to pH 4 using 2 M HCl and extracted with dichloromethane (5×150 mL). The organics were dried (MgSO$_4$) and the solvent removed in vacuo. Column chromatography (ethyl acetate:heptane 4:1→ethyl acetate:methanol) gave a brown solid. This was dissolved in ethyl acetate, heptane was added, and the mixture was stirred overnight. Solvent was removed by syringe to give product as a pale brown solid, 17 mmol, 61%.

$^1$H NMR (400 MHz, CDCl$_3$): δ7.54–7.52 (1H, m); 7.46–7.44 (1H, m); 7.28–7.19 (2H, m); 6.66 (1H, s); 3.88 (2H, s).

What is claimed is:

1. A compound of Formula I

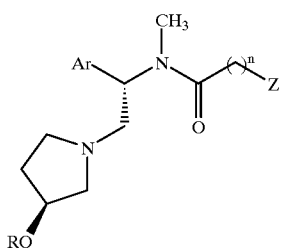

I or a pharmaceutically acceptable salt thereof wherein:
   Ar is phenyl unsubstituted or substituted with from 1 to 5 substituents selected from methyl, hydroxy, methoxy, and halogen;
   n is an integer of from 0 to 1;
   Z is 2-benzofuranyl, 3-benzofuranyl, 4-benzofuranyl, 5-benzofuranyl, 6-benzofuranyl, 7-benzofuranyl, when n is 1;
   and
   R is hydrogen or methyl.

2. A compound according to claim 1 wherein Z is 2-benzofuranyl, 3-benzofuranyl, 4-benzofuranyl, 5-benzofuranyl, 6-benzofuranyl, 7-benzofuranyl, and n is 1.

3. A pharmaceutical composition which comprises a therapeutically effective amount of a compound according to claim 1, of Formula I in combination with a pharmaceutically acceptable carrier in unit dosage form.

4. A method of treating arthritis which comprises administering a therapeutically effective amount of a compound according to claim 1 to a mammal in need of said treatment.

5. A method of treating pain which comprises administering a therapeutically effective amount of a compound according to claim 1 to a mammal in need of said treatment.

6. A method of treating inflammation which comprises administering a therapeutically effective amount of a compound according to claim 1 to a mammal in need of said treatment.

7. A method of treating migraine which comprises administering a therapeutically effective amount of a compound according to claim 1 to a mammal in need of said treatment.

8. A method of treating inflammatory disorders of the gastrointestinal tract which comprises administering a therapeutically effective amount of a compound according to claim 1 to a mammal in need of said treatment.

9. A method of treating irritable bowel syndrome which comprises administering a therapeutically effective amount of a compound according to claim 1 to a mammal in need of said treatment.

10. A method of treating psoriasis which comprises administering a therapeutically effective amount of a compound according to claim 1 to a mammal in need of said treatment.

11. A process for the preparation of a compound of Formula I above which comprises:
   a.) converting styrene oxide into a diamine of formula 3

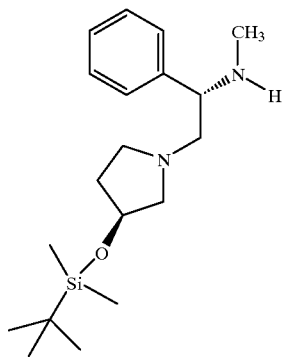

3 b.) coupling the diamine with an acid using a suitable coupling reagent to produce the corresponding amide;
   c.) removing the protecting group to produce the compound of formula 1, and converting it, if desired, to the pharmaceutically acceptable thereof.

12. A compound according to claim 1 and selected from:
   2-Benzofuran-4-yl-N-[2-(3-hydroxy-pyrrolidin-1-yl)-1-phenyl-ethyl]-N-methyl-acetamide;
   2-Benzofuran-3-yl-N-[2-(3-hydroxy-pyrrolidin-1-yl)-1-phenyl-ethyl]-N-methyl-acetamide; and
   2-Benzofuran-4-yl-N-[2-(3-methoxy-pyrrolidin-1-yl)-1-phenyl-ethyl]-N-methyl-acetamide.

* * * * *